United States Patent
Brown et al.

(10) Patent No.: US 9,426,400 B2
(45) Date of Patent: Aug. 23, 2016

(54) METHOD AND APPARATUS FOR HIGH SPEED ACQUISITION OF MOVING IMAGES USING PULSED ILLUMINATION

(71) Applicant: KLA-Tencor Corporation, Milpitas, CA (US)

(72) Inventors: David L. Brown, Los Gatos, CA (US); Yung-Ho Chuang, Cupertino, CA (US); Yury Yuditsky, Mountain View, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/096,911

(22) Filed: Dec. 4, 2013

(65) Prior Publication Data

US 2014/0158864 A1 Jun. 12, 2014

Related U.S. Application Data (60) Provisional application No. 61/735,427, filed on Dec. 10, 2012.

(51) Int. Cl.
*H04N 5/374* (2011.01)
*H04N 5/225* (2006.01)
*G01N 21/956* (2006.01)

(52) U.S. Cl.
CPC ........... *H04N 5/3742* (2013.01); *H04N 5/3743* (2013.01); *G01N 2021/95676* (2013.01); *H04N 5/2256* (2013.01)

(58) Field of Classification Search
CPC .. H04N 5/3742; H04N 5/3743; H04N 5/2256
USPC ........................................................ 348/295
See application file for complete search history.

(56) References Cited

U.S. PATENT DOCUMENTS 3,755,704 A 8/1973 Spindt et al.
3,870,917 A 3/1975 Cuny
(Continued)

FOREIGN PATENT DOCUMENTS

EP 0746871 B1 5/2000
EP 0602983 B1 6/2000
(Continued)

OTHER PUBLICATIONS

Tobin, Kenneth W., "Inspection in Semiconductor Manufacturing", Webster's Encyclopedia of Electrical and Electronic Engineering, vol. 10, pp. 242-262, Wiley & Sons, NY, NY, 1999.
(Continued)

*Primary Examiner* — Christopher K Peterson
(74) *Attorney, Agent, or Firm* — Bever, Hoffman & Harms, LLP (57) ABSTRACT

A method of operating an image sensor with a continuously moving object is described. In this method, a timed delay integration mode (TDI-mode) operation can be performed during an extended-time illumination pulse. During this TDI-mode operation, charges stored by pixels of the image sensor are shifted only in a first direction, and track the image motion. Notably, a split-readout operation is performed only during non-illumination. During this split-readout operation, first charges stored by first pixels of the image sensor are shifted in the first direction and second charges stored by second pixels of the image sensor are concurrently shifted in a second direction, the second direction being opposite to the first direction.

20 Claims, 6 Drawing Sheets

(56) References Cited

U.S. PATENT DOCUMENTS

| | | |
|---|---|---|
| 3,947,707 A | 3/1976 | Shannon |
| 4,099,198 A | 7/1978 | Howorth et al. |
| 4,210,922 A | 7/1980 | Shannon |
| 4,275,326 A | 6/1981 | Houtkamp |
| 4,348,690 A | 9/1982 | Jastrzbski |
| 4,467,189 A | 8/1984 | Tsuchiya |
| 4,555,731 A | 11/1985 | Zinchuk |
| 4,760,031 A | 7/1988 | Janesick |
| 5,054,683 A | 10/1991 | Haisma et al. |
| 5,120,949 A | 6/1992 | Tomasetti |
| 5,227,313 A | 7/1993 | Gluck et al. |
| 5,315,126 A | 5/1994 | Field |
| 5,376,810 A | 12/1994 | Hoenk et al. |
| 5,428,392 A * | 6/1995 | Castro et al. ............... 348/295 |
| 5,563,702 A | 10/1996 | Emery et al. |
| 5,717,518 A | 2/1998 | Shafer et al. |
| 5,719,069 A | 2/1998 | Sparks |
| 5,731,584 A | 3/1998 | Beyne |
| 5,760,899 A | 6/1998 | Eismann |
| 5,852,322 A | 12/1998 | Speckbacher |
| 5,940,685 A | 8/1999 | Loomis et al. |
| 5,999,310 A | 12/1999 | Shafer et al. |
| 6,013,399 A | 1/2000 | Nguyen |
| 6,162,707 A | 12/2000 | Dinh |
| 6,201,601 B1 | 3/2001 | Vaez-Iravani et al. |
| 6,271,916 B1 | 8/2001 | Marxer et al. |
| 6,278,119 B1 | 8/2001 | Nikzad et al. |
| 6,285,018 B1 | 9/2001 | Aebi et al. |
| 6,297,879 B1 | 10/2001 | Yang et al. |
| 6,307,586 B1 | 10/2001 | Costello |
| 6,362,484 B1 | 3/2002 | Beyne |
| 6,373,869 B1 | 4/2002 | Jacob |
| 6,403,963 B1 | 6/2002 | Nikzad |
| 6,545,281 B1 | 4/2003 | McGregor |
| 6,608,676 B1 | 8/2003 | Zhao et al. |
| 6,711,283 B1 | 3/2004 | Soenksen |
| 6,837,766 B2 | 1/2005 | Costello |
| 7,005,637 B2 | 2/2006 | Costello et al. |
| 7,039,157 B2 | 5/2006 | Fuji et al. |
| 7,126,699 B1 | 10/2006 | Wihl et al. |
| 7,130,039 B2 | 10/2006 | Vaez-Iravani et al. |
| 7,136,159 B2 | 11/2006 | Tsai et al. |
| 7,283,166 B1 | 10/2007 | Billman |
| 7,313,155 B1 | 12/2007 | Mu |
| 7,345,825 B2 | 3/2008 | Chuang et al. |
| 7,446,474 B2 | 11/2008 | Maldonado |
| 7,465,935 B2 | 12/2008 | Urano et al. |
| 7,525,649 B1 | 4/2009 | Leong et al. |
| 7,528,943 B2 | 5/2009 | Brown et al. |
| 7,586,108 B2 | 9/2009 | Nihtianov et al. |
| 7,609,309 B2 | 10/2009 | Brown et al. |
| 7,741,666 B2 | 6/2010 | Nozaki et al. |
| 7,750,280 B2 | 7/2010 | Hwang et al. |
| 7,791,170 B2 | 9/2010 | Chiang et al. |
| 7,928,382 B2 | 4/2011 | Hatakeyama et al. |
| 7,952,633 B2 | 5/2011 | Brown et al. |
| 7,985,658 B2 | 7/2011 | Lei et al. |
| 7,999,342 B2 | 8/2011 | Hsu et al. |
| 8,138,485 B2 | 3/2012 | Nihtianov et al. |
| 8,309,443 B2 | 11/2012 | Tanaka et al. |
| 8,450,820 B2 | 5/2013 | Nanver |
| 8,455,971 B2 | 6/2013 | Chen et al. |
| 8,513,587 B2 | 8/2013 | Wang et al. |
| 8,624,971 B2 | 1/2014 | Brown et al. |
| 8,629,384 B1 | 1/2014 | Biellak et al. |
| 8,754,972 B2 | 6/2014 | Brown et al. |
| 8,891,079 B2 | 11/2014 | Zhao et al. |
| 2001/0017344 A1 | 8/2001 | Aebi |
| 2002/0191834 A1 | 12/2002 | Fishbaine |
| 2003/0222579 A1 | 12/2003 | Habib et al. |
| 2004/0021061 A1 | 2/2004 | Bijkerk |
| 2004/0056279 A1 | 3/2004 | Niigaki |
| 2004/0227070 A1 | 11/2004 | Bateman et al. |
| 2005/0167575 A1 | 8/2005 | Benz et al. |
| 2005/0196059 A1 | 9/2005 | Inoue et al. |
| 2005/0264148 A1 | 12/2005 | Maldonado et al. |
| 2006/0054778 A1 | 3/2006 | Suhling |
| 2006/0055321 A1 | 3/2006 | Maldonado et al. |
| 2006/0069460 A1 | 3/2006 | Smith et al. |
| 2006/0170324 A1 | 8/2006 | Machuca |
| 2006/0188869 A1 * | 8/2006 | Zeskind et al. ............... 435/4 |
| 2007/0002465 A1 | 1/2007 | Chuang et al. |
| 2007/0034987 A1 | 2/2007 | Costello et al. |
| 2007/0064135 A1 * | 3/2007 | Brown et al. ............... 348/311 |
| 2007/0103769 A1 | 5/2007 | Kuwabara |
| 2007/0291810 A1 | 12/2007 | Luo et al. |
| 2008/0044932 A1 | 2/2008 | Samoilov et al. |
| 2008/0182092 A1 | 7/2008 | Bondokov et al. |
| 2008/0267241 A1 | 10/2008 | Brown et al. |
| 2008/0315092 A1 | 12/2008 | Kley |
| 2008/0315121 A1 | 12/2008 | Nihtianov et al. |
| 2009/0021717 A1 | 1/2009 | Nihtianov et al. |
| 2009/0091752 A1 | 4/2009 | Terasawa et al. |
| 2009/0125242 A1 | 5/2009 | Choi |
| 2009/0128912 A1 | 5/2009 | Okada |
| 2009/0168152 A1 | 7/2009 | Gelernt et al. |
| 2010/0102213 A1 | 4/2010 | Garris |
| 2010/0148667 A1 | 6/2010 | Niigaki et al. |
| 2010/0301437 A1 | 12/2010 | Brown et al. |
| 2011/0101219 A1 | 5/2011 | Uchiyama et al. |
| 2011/0116077 A1 | 5/2011 | Chuang et al. |
| 2011/0169116 A1 | 7/2011 | Nanver et al. |
| 2011/0234790 A1 | 9/2011 | True |
| 2011/0256655 A1 | 10/2011 | Nikzad et al. |
| 2011/0261354 A1 | 10/2011 | Sinfield |
| 2011/0291109 A1 | 12/2011 | Wraback |
| 2012/0012811 A1 | 1/2012 | DeFlumere |
| 2012/0012957 A1 | 1/2012 | Larsen |
| 2012/0081684 A1 | 4/2012 | Den Oef et al. |
| 2012/0132823 A1 | 5/2012 | Menge |
| 2012/0160993 A1 | 6/2012 | Nevet |
| 2012/0170021 A1 | 7/2012 | Walsh |
| 2012/0228485 A1 | 9/2012 | Iwakiri et al. |
| 2013/0016346 A1 | 1/2013 | Romanovsky et al. |
| 2013/0017205 A1 | 1/2013 | Giaccia et al. |
| 2013/0056843 A1 | 3/2013 | Lee |
| 2013/0082241 A1 | 4/2013 | Kub et al. |
| 2013/0148112 A1 | 6/2013 | Chuang et al. |
| 2013/0264481 A1 | 10/2013 | Chern et al. |
| 2013/0270663 A1 | 10/2013 | Lin et al. |
| 2013/0320211 A1 | 12/2013 | Park et al. |
| 2014/0111799 A1 | 4/2014 | Lei et al. |
| 2014/0203386 A1 | 7/2014 | Bui |
| 2014/0204963 A1 | 7/2014 | Chuang et al. |
| 2014/0246595 A1 | 9/2014 | Menge |
| 2014/0291493 A1 | 10/2014 | Chuang |
| 2014/0362203 A1 | 12/2014 | Delaney |
| 2015/0177159 A1 | 6/2015 | Brown et al. |
| 2015/0200216 A1 | 7/2015 | Muramatsu et al. |
| 2015/0275393 A1 | 10/2015 | Bondokov et al. |
| 2015/0294998 A1 | 10/2015 | Nihtianov |

FOREIGN PATENT DOCUMENTS

| | | |
|---|---|---|
| EP | 1939917 A2 | 7/2008 |
| EP | 2346094 A1 | 7/2011 |
| JP | H05511287 A | 1/1993 |
| JP | 10-171965 A | 6/1998 |
| JP | 2003043533 A | 2/2003 |
| JP | 2004031452 A | 1/2004 |
| JP | 2007249092 A | 9/2007 |
| JP | 2007298932 A | 11/2007 |
| JP | 2009117454 A | 5/2009 |
| KR | 100688497 | 3/2007 |
| KR | 100826407 | 5/2008 |
| RU | 2297070 C2 | 4/2007 |
| WO | 9532518 A1 | 11/1995 |
| WO | 9617372 A1 | 6/1996 |
| WO | 2007035858 A2 | 3/2007 |

(56) References Cited

FOREIGN PATENT DOCUMENTS

| WO | 2011091159 | 7/2011 |
|---|---|---|
| WO | 2014067754 | 5/2014 |

OTHER PUBLICATIONS

International Search Report and Written Opinion dated Mar. 31, 2014 for PCT/US2013/074124, filed Dec. 10, 2013 in the name of KLA-Tencor Corporation.

Sarubbi F et al: "Pure boron-doped photodiodes: a solution for radiation detection in EUV lithography", Proceedings of the 38th European Solid-State Device Research Conference: Edinburgh International Conference Centre, Endiburgh, Scotland, UK, Sep. 15-19, 2008, Piscataway, NJ: IEE, US, Sep. 15, 2008, pp. 278-281.

Sobieski, Stanley, "Intensified Charge Coupled Devices for Ultra Low Light Level Imaging", NASA, Goddard Space Flight Center, SPIE vol. 78 (1976) Low Light Level Devices, pp. 73-77.

Certified copy of priority document U.S. Appl. No. 61/720,700, filed Oct. 31, 2012 corresponding to PCT/EP2013/071080 filed Oct. 9, 2013, pp. 1-44.

Sarubbi, F. et al. "Chemical Vapor Deposition of α-Boron Layers on Silicon for Controlled Nanometer-Deep p+ n Junction Formation", J. Electron. Mat., vol. 39, No. 2, Feb. 2010, pp. 162-173.

Nikzad, Shouleh et al., Delta-doped CCDs: High QE with long-term stability at UV and visible wavelengths, SPIE vol. 2198 (1994), pp. 907-915.

Hecht, Eugene, Optics, 4th Edition, India: Pearson Education Pte, Ltd. reprint 2004, 4 pages.

Hecht, Eugene, Optics, 2nd Edition, Adelphi University, 1987, Addison-Wesley Publishing Co., Inc., 3 pages.

Martinelli, Ramon U. "Infrared Photoemission from Silicon", Applied Physics Letters, vol. 16, No. 7, Apr. 1, 1970, pp. 261-262.

Martinelli, Ramon U. "Reflection and Transmission Secondary Emission from Silicon", Applied Physics Letters, vol. 17, No. 8, Oct. 15, 1970, pp. 313-314.

Henderson, Brian S. "Study of Negative Electron Affinity GaAs Photocathodes", Department of Physics and Astronomy, Rice University, Houston, TX, Aug. 7, 2009, 18 pages.

Allen, F. G. et al. "Work Function, Photoelectric Threshold, and Surface States of Atomically Clean Silicon", Physical Review, vol. 127, No. 1, Jul. 1, 1962, pp. 150-158.

Howorth, J. R. et al. "Transmission silicon photoemitters and electron multipliers," Journal of Physics D: Applied Physics, vol. 9, No. 5, Apr. 1, 1976, pp. 785-794.

Fu et al. "Optimizing GaN photocathode structure for higher quantum efficiency", Optik, vol. 123, No. 9, May 2012, pp. 756-768.

KLA-Tencor Corporation; PCT International Search Report dated Dec. 8, 2015 for Application No. PCT/US2015/047307, 3 pages.

KLA-Tencor Corporation; PCT International Search Report dated Dec. 29, 2015 for Application No. PCT/US2015/051538, 3 pages.

Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.

Itzler, Mark et al., "InP-based Geiger-mode avalanche photodiode arrays for three-dimensional imaging at 1.06 μm", Proceedings of SPIE, vol. 7320 (2000), 12 pages.

Niclass, Cristiano et al., "Design and Characterization of a CMOS 3-D Image Sensor Based on Single Photon Avalanche Diodes", IEEE Journal of Solid-State Circuits, vol. 40, No. 9, Sep. 2005, 8 pages.

Paetzel, Rainer et al., "Activation of Silicon Wafer by Excimer Laser" 18th IEEE Conf. Advanced Thermal processing of Semiconductors—RTP 2010, 5 pages.

Stevanovic, Nenad et al., "A CMOS Image Sensor for High-Speed Imaging", 2000 IEEE Int'l. Conference Solid-State Circuits, 3 pages.

Dulinski, Wojciech et al., "Tests of a backside illuminated monolithic CMOS pixel sensor in an HPD set-up", Nuclear Instruments and Methods in Physics Research a 546 (2005) 274-280, 7 pages.

Sarubbi, F et al, "Pure boron-doped photodiodes: a solution for radiation detection in EUV lithography", Proceedings of the 38th EP Solid-State Device Research Conf., Edinburgh Int'l Conf. Centre, Endiburgh, Scotland, UK, Sep. 15-19, 2008, Piscataway, NJ: IEEE, US, pp. 278-281.

Fu, Xiaoqian, "Higher Quantum Efficiency by Optimizing GaN Photocathode Structure", 978-1-4244-6644-3/10/ ©2010 IEEE, pp. 234-235.

Sakic, Agata, "Boron-layer silicon photodiodes for high-efficiency low-energy electron detection", Solid-State Electronics 65-66 (2011), pp. 38-44.

Omatsu, Takashige et al., "High repetition rate Q-switching performance in transversely diode-pumped Nd doped mixed gadolinium yttrium vanadate bounce laser", Optics Express vol. 14, Issue 7, pp. 2727-2734, Apr. 3, 2006.

Nagao, Cathod Technologies for Field Emission Displays, IEJ Trans 2006; 1:171-178, 8 pgs.

Fowler, Electron Emission in Intense Electric Fields, Mar. 31, 1928, 9 pgs.

Neo, Electron Optical Properties of Microcolumn with Field Emitter, JJAP 52 (2013) 036603, 5 pgs.

Sato, Fabrication and characterization of HfC coated . . ., J. Vac. Sci. Technol. B 2194), published Jul. 31, 2003, 5 pgs.

Nagao, Fabrication of a Field Emitter Array with a Built-In Einzel Lens, JJAP 48 (2008) 06FK02, 4 pgs.

Rakhshandehroo, Fabrication of a self-aligned silicon field emission . . ., JVSTB, 16, 765 (1998); doi: 10.1116/1,589900, 6 pgs.

Rakhshandehroo, Field emission from gated Si emitter tips with precise . . ., JVSTB, 15, 2777 (1997); doi: 10.1116/1.589726, 6 pgs.

Ding, Field Emission from Silicon, MIT 2001, 277 pgs.

Koike, Field Emitter Equipped With a Suppressor to Control Emission Angel, IEEE Electron Device Letters, vol. 34, No. 5, May 2013, 3 pgs.

Unknown, Field Emitter Review, 7 pgs in Japanese.

Fanton, J. T., et al., "Multiparameter Measurements of Thin Films Using beam-profile reflectometry", Journal of Applied Physics, vol. 73, No. 11, p. 7035 (1993).

Serbun, Stable field emission of single B-doped . . ., JVSTB, 31, 02B101 (2013); doi: 10.1116/1.4765088, 7 pgs.

Armstrong, The Quest for the Ultimate Vacuum Tube, Spectrum IEEE, Dec. 2015, 4 pgs.

Utsumi, Vacuum Microelectrnoics: What's New and Exciting, IEEE vol. 38, No. 10, Oct. 1991, 8 pgs.

\* cited by examiner

| | TDI Operation Sensor Mode 1 320 | Split-Readout Operation Sensor Mode 2 321 |
|---|---|---|
| P1b | ↑ | ↓ |
| P2b | ↑ | ↓ |
| P3b | ↑ | ↓ |
| P1b | ↑ | ↓ |
| P2b | ↑ | ↓ |
| P3b | ↑ | ↓ |
| P1b | ↑ | ↓ |
| P2b | ↑ | ↓ |
| P3b | ↑ | ↓ |
| P1a | ↑ | ↑ |
| P2a | ↑ | ↑ |
| P3a | ↑ | ↑ |
| P1a | ↑ | ↑ |
| P2a | ↑ | ↑ |
| P3a | ↑ | ↑ |
| P1a | ↑ | ↑ |
| P2a | ↑ | ↑ |
| P3a | ↑ | ↑ |

METHOD AND APPARATUS FOR HIGH SPEED ACQUISITION OF MOVING IMAGES USING PULSED ILLUMINATION

RELATED APPLICATIONS

This application claims priority of U.S. Provisional Patent Application 61/735,427, entitled "Method And Apparatus For High Speed Acquisition Of Moving Images Using Pulsed Illumination" filed Dec. 10, 2012.

BACKGROUND OF THE INVENTION

1. Field of the Invention

The invention relates to systems configured to use both timed delay integration and pulsed illumination while owing high-speed image scanning.

2. Related Art

Time delay integration (TDI) is an imaging process that produces a continuous image of a moving object that can be much larger than the field of view of the imaging hardware. In a TDI system, image photons are converted to photocharges in a sensor comprising an array of pixels. As the object is moved, the photocharges are shifted from pixel to pixel down the sensor, parallel to the axis of movement. By synchronizing the photocharge shift rate with the velocity of the object, the TDI can integrate signal intensity at a fixed position on the moving object to generate the image. The total integration time can be regulated by changing the speed of the image motion and providing more/less pixels in the direction of the movement. In conventional TDI inspection systems, the readout circuits are positioned on one side of the sensor to read out the integrated signal. TDI inspection systems can be used for inspecting wafers, masks, and/or reticles.

In a system with continuous illumination and a moving object, the TDI must be precisely synchronized to the image motion so that the recorded image is not blurred. One disadvantage of this system is that the readout of the sensor can be in only one direction, i.e. in the direction corresponding to the image motion, and must operate at the same scan rate as the object during the illumination pulse. In a system with pulsed illumination and a moving object, the image can be collected almost instantly over the entire sensor area. The image can then be read out along both sides of the sensor, thereby effectively doubling the readout speed. The readout line rate can also be faster than the image scan rate without compromising the final image quality, which can further increase readout speed. A critical disadvantage of this system is that the illumination pulse must be very short so that the moving image does not produce blur during the exposure time. As the pulsed illumination time approaches the sensor line period, the image motion will start to cause significant blur, and the image will degrade severely beyond that threshold. Another disadvantage of this system using very short pulses is that the image information at defective pixel locations on the sensor cannot be recovered.

Therefore, a need arises for a method and apparatus that provides a continuously moving object, pulsed illumination, fast readout capability, and recovery of image information where sensor pixels are defective.

SUMMARY

A method of operating an image sensor with a continuously moving object is described. In this method, a timed delay integration mode (TDI-mode) operation can be performed during an extended-time illumination pulse. During this TDI-mode operation, all charges stored by pixels of the image sensor are shifted only in a first direction, and track the image motion. Notably, a split-readout operation is performed only during non-illumination. During this split-readout operation, first charges stored by first pixels of the image sensor are shifted in the first direction and second charges stored by second pixels of the image sensor are concurrently shifted in a second direction, the second direction being opposite to the first direction.

The TDI-mode operation is synchronized with the illumination pulse. In one embodiment, the TDI-mode operation is triggered to start within one clock period of the illumination pulse using electronic or optical sychronization. The time of the TDI-mode operation includes a period of the pulsed illumination. During the split-readout operation, the image sensor charge movement is not synchronized with the image motion. In one embodiment, performing the split-readout operation can include a parallel readout of a plurality of sensor output channels.

An idle operation can be provided before the TDI-mode operation and the split-readout operation (and in one embodiment, also between the TDI-mode operation and the split-readout operation) in order to facilitate synchronization of object and sensor readout, or to reduce power consumption of the detection system. In one embodiment, an illumination interval can include a plurality of illumination pulses. Analyzing the pixel outputs corresponding to the plurality of illumination pulses that extend over one or more TDI line periods can improve the image quality near pixel defects on the image sensor.

A system for inspection or metrology is also described. This system includes a pulsed illumination source, an image sensor, optical components, and a processor. The illumination pulse may be similar to or longer than the line period of the sensor. The optical components are configured to direct pulsed illumination from the pulsed illumination source to an object, and direct reflected light from the object to the image sensor. The processor is configured to operate the image sensor. A configuration includes performing a process including the TDI-mode operation and the split-readout operation, as described above.

DETAILED DESCRIPTION OF THE DRAWINGS

Figure 1:
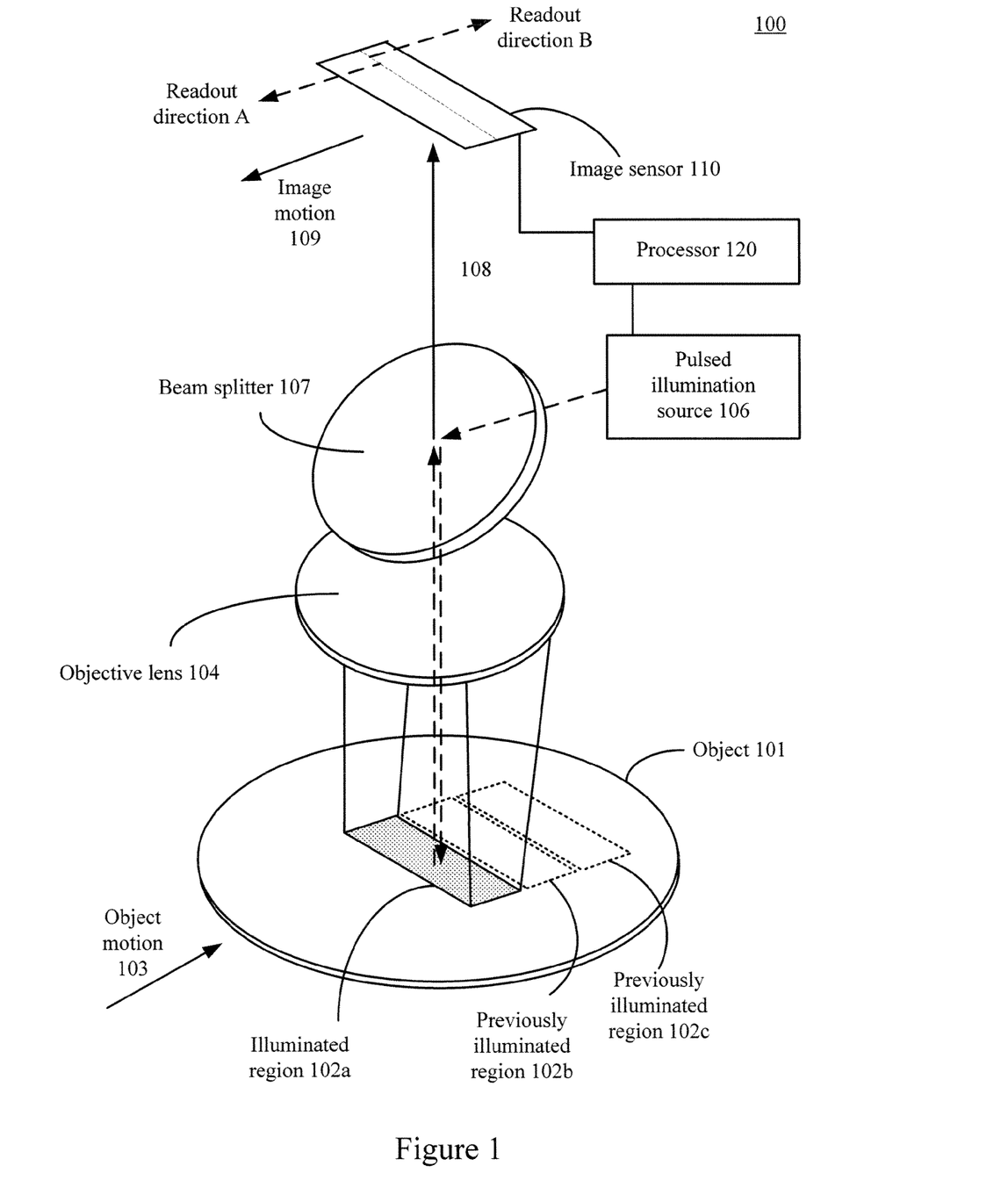
FIG. 1 illustrates an exemplary scanning inspection system using pulsed illumination with a continuously moving object.

FIG. 1 illustrates an exemplary system 100 configured to use a pulsed illumination source 106 with a continuously moving object 101, such as a wafer, mask, or reticle. Advantageously, pulsed illumination 106 can be a long pulse. Exemplary sources for pulsed illumination 106 can include a Q-switched laser or a pulsed lamp. A Q-switched laser uses a variable attenuator inside the laser's optical resonator to produce light pulses with extremely high peak power. These light pulses are much higher than those produced by the same laser operating in continuous mode. A pulsed lamp could be implemented by a deep ultraviolet (DUV) excimer or an extreme ultraviolet (EUV) source. In one preferred embodiment, the pulse duration is close to or longer than the line period of the TDI. For a line period of 1 microsecond, suitable illumination could be near 500 ns, or beyond 10's or even 100's of microseconds, with significant benefit from the described method of this invention.

In system 100, a beam splitter 107 would direct illumination pulses from pulsed illumination source 106 to an objective lens 104, which would focus that light onto object 101. Reflected light from object 101 would then be directed to an image sensor 110. Note that other well-known optical components for directing and focusing of the light are not shown for simplicity in FIG. 1. For example, U.S. Pat. No. 5,717,518, which issued Feb. 10, 1998, and U.S. patent application Ser. No. 13/554,954, which was filed Jul. 9, 2012, both of which are incorporated by reference herein, describe exemplary optical components that can be used in system 100. A processor 120, which is coupled to image sensor 110, is configured to provide synchronization of illumination pulses from pulsed illumination source 106 with control and data signals to and from image sensor 110 as well as analysis of the image data (described in detail below). In the above-described configuration, object 101 has an object motion 103 and image sensor 110 has an image motion 109.

In accordance with one aspect of system 100, because of object motion 103, the illuminated region will continuously move across object 101 as indicated by illuminated region 102a (e.g. time period N), previously illuminated region 102b (e.g. time period N–1), and previously illuminated region 102c (e.g. time period N–2). Each of illuminated regions 102a, 102b, and 102c can be a thin rectangular-shaped region (not shown to scale for ease of viewing). Note the regions are shown separated for clarity, but may overlap to provide 100% imaging coverage, or for additional redundancy and performance during defect detection.

Figure 2A:
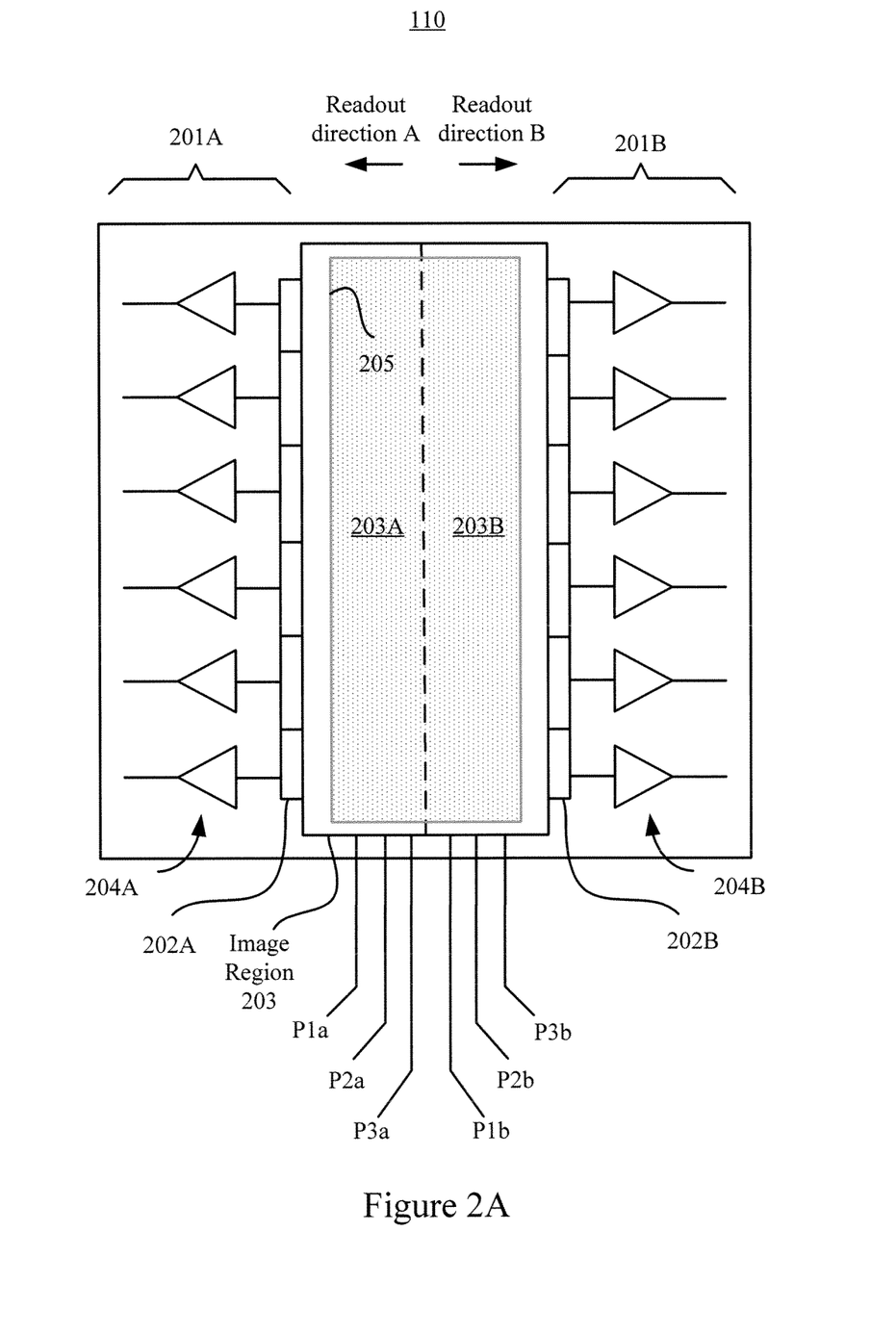
FIG. 2A illustrates an exemplary image sensor having two sides, which can be operated independently.

FIG. 2A illustrates an exemplary split-readout image sensor 110 including two sets of readout circuits 201A and 201B positioned on either side of an image region 203. Readout circuits 201A and 201B can include serial registers 202A and 202B and readout amplifiers 204A and 204B, as well as other components such as transfer gates. Exemplary embodiments of readout circuits 201A and 201B, as well as other components of sensor 110 are described in U.S. Pat. No. 7,609,309, entitled "Continuous Clocking of TDI Sensors", issued Oct. 27, 2009, which is incorporated by reference herein. Image region 203 is a two-dimensional (2D) array of pixels, and each line of the image is read out concurrently in each direction A and B. Each line is then read out one pixel at a time in the simplest case. Therefore, in preferred embodiments, the serial registers 202A and 202B can be divided into a plurality of register segments (e.g. FIG. 2A shows each serial register being divided into six segments, thereby allowing parallel read out using a plurality of amplifiers 204A and 204B).

Notably, readout circuits 201A and 201B can be operated independently, thereby allowing image sensor 110 to provide two readout directions A and B. In a split-readout mode, each side of image region 203 (i.e. sides 203A and 203B) can be synchronously clocked to read out one image line into their respective output channels. In one embodiment, image region 203 may have 1000 lines, each line formed by a column of pixels. Therefore, during the split-readout mode, 500 lines could be read out in direction A and, concurrently, 500 lines could be read out in direction B.

Figure 2B:
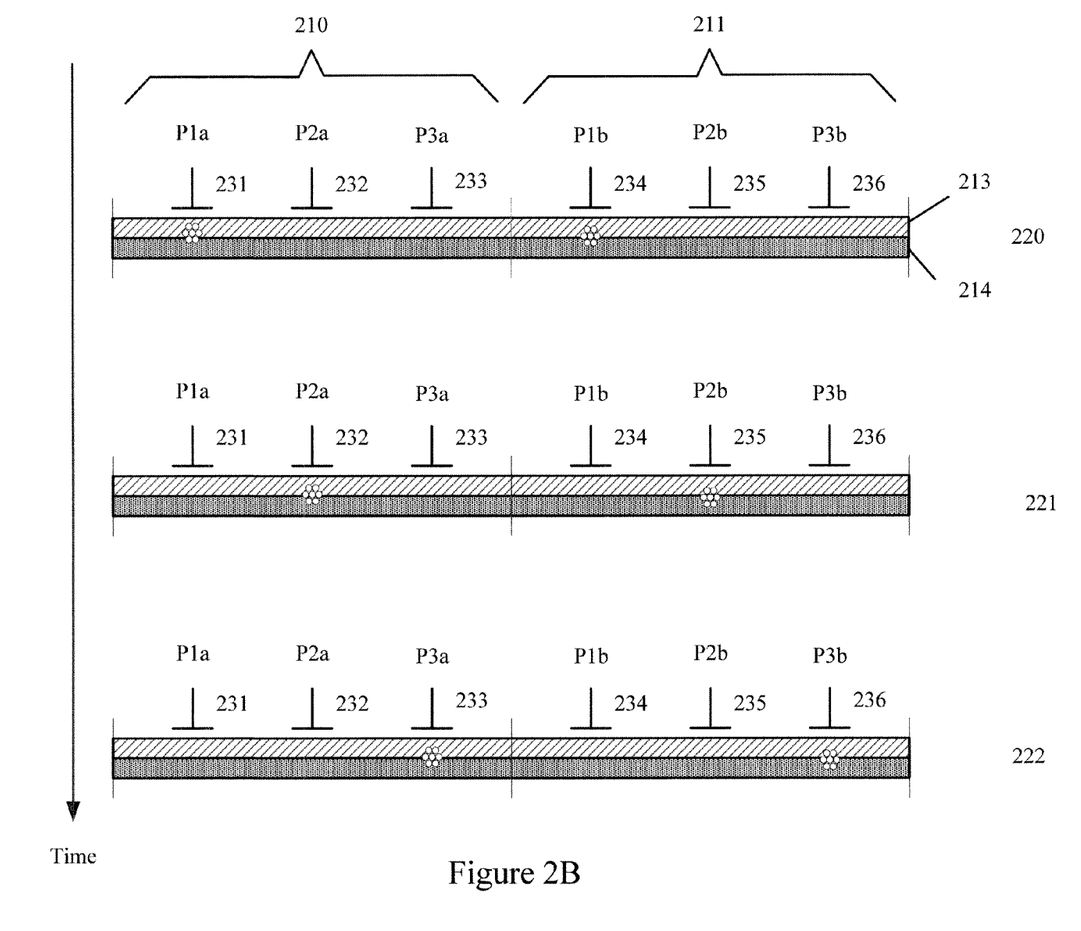
FIG. 2B illustrates the operation of exemplary CCD gates, which can be used for the image sensor.

This split-readout mode is possible based on the timed activation of the charge-coupled device (CCD) drivers in image sensor 110. For example, a plurality of CCD drivers P1a, P2a, P3a, P1b, P2b, and P3b can be used to provide phases. As shown in FIG. 2B, CCD drivers P1a, P2a, P3a, P1b, P2b, and P3b can be characterized as driving sets of gate electrodes (hereinafter gates), each set having six gates. In one preferred embodiment of image sensor 110, three gates are provided for each pixel to provide three phases. In FIG. 2B, two pixels 210 and 211 are shown, wherein gates 231, 232, and 233 are positioned over pixel 210 and gates 234, 235, and 236 are positioned over pixel 211. In image sensor 110, pixels 210 and 211 are aligned along the read-out axis to form part of a column of the 2D array of pixels forming image region 203.

Image region 203 can be implemented as an optical sensor or a photocathode. In one optical sensor embodiment, image region 203 can include a photo-sensitive p-type silicon substrate 214 and an n-type buried channel 213. The electrostatic forces in silicon substrate 214 are determined by the voltage level applied to a particular gate by a clock input signal (e.g. one of clock signals from CCD drivers P1a, P2a, P3a, P1b, P2b, and P3b). High level voltages induce the formation of a potential "well" beneath the gate, whereas low level voltages form a potential barrier to electron movement. To ensure that charge from one pixel is not mixed with other pixels, a gate voltage is driven high when an adjacent gate voltage is driven low (described in further detail in reference to FIGS. 3A and 3B). At an initial state at time 220, gates 231 and 234 of pixels 210 and 211, respectively, have high level voltages that form potential wells with integrated charge (i.e. electrons), and gates 232, 233 (of pixel 210) and 235, 236 (of pixel 211) have low level voltages that form potential barriers. At a subsequent time 221, gates 232 and 235 of pixels 210 and 211, respectively, have high level voltages that form potential wells with integrated charge (i.e. electrons), and gates 231, 233 (of pixel 210) and 234, 236 (of pixel 211) have low level voltages that form potential barriers. At yet a subsequent time 222, gates 233 and 236 of pixels 210 and 211, respectively, have high level voltages that form potential wells with integrated charge (i.e. electrons), and gates 231, 232 (of pixel 210) and 234, 235 (of pixel 211) have low level voltages that form potential barriers. Note that adjacent gates when shifting charge preferably both have a high level voltage for a short time to facilitate charge transfer. (FIG. 3A, which is described below) shows this timing overlap.) Thus from time 220 to time 222, the charge is shifted from left to right, i.e. from pixel 210 to pixel 211. This directional shifting of charge can be advantageously modified during modes of the inspection system, as described in reference to FIG. 3.

Figure 3A:
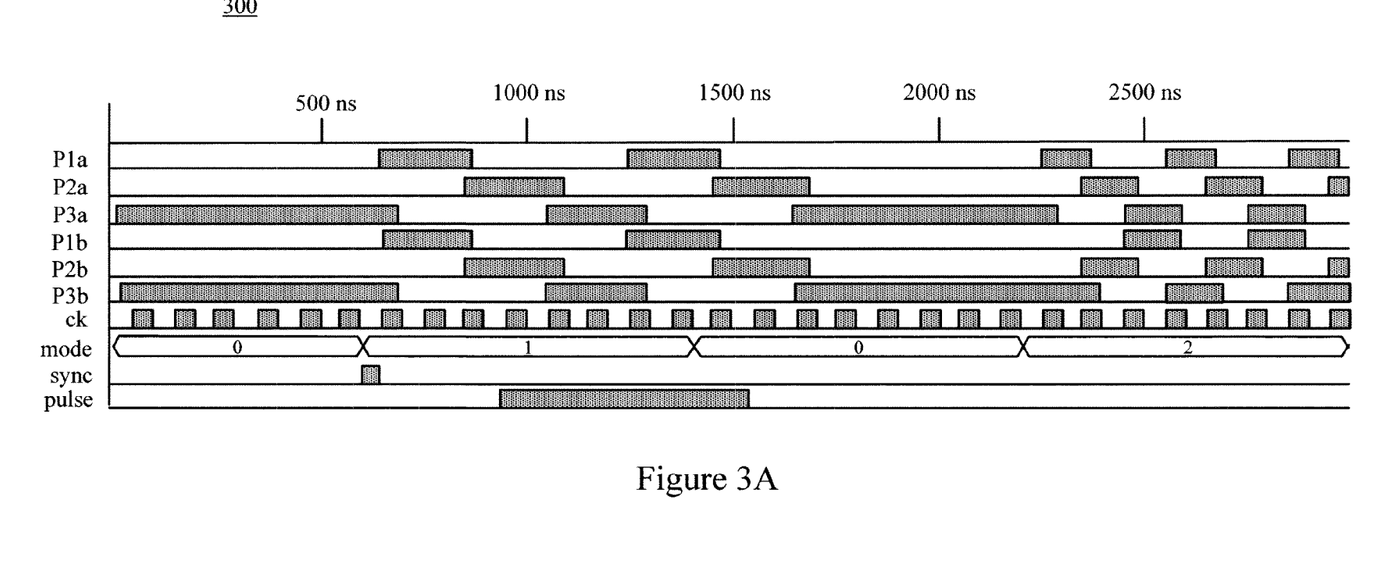
FIG. 3A illustrates an exemplary timing diagram, with three distinct operating modes, for a three-phase CCD in a system with pulsed illumination.

FIG. 3A illustrates an exemplary timing diagram 300 indicating signals output by CCD drivers P1a, P2a, P3a, P1b, P2b, and P3b, clock signals (ck), an external synchronization pulse (sync), and a pulsed illumination time (pulse). Note that the start and stop of a voltage transition of each signal output by the CCD drivers can be synchronized to the clock signals ck. The external synchronization pulse sync triggers a three-mode cycle (one complete cycle being shown in FIG. 3A). In the example of FIG. 3A, one laser pulse is provided during each cycle.

The three sensor modes are indicated in FIG. 3A as "0", "1", and "2". Sensor mode 1 is TDI-mode operation in which the laser pulse occurs and therefore an image of the illuminated region of the object can be generated. In one embodiment, the pulse duration may be close to or longer than the line period of the high-speed TDI, which could be, for example, 1 microsecond. Note that because the illumination pulse can be long (e.g. more than 1 microsecond), a fixed point on the image will shift across one or more sensor pixels. Therefore, consecutive clocking of CCD drivers P1a/P1b, P2a/P2b, and P3a/P3b (shown in FIG. 3) can be performed to ensure that the generated charge in the image region is shifted along with the image, to provide TDI-mode operation and ensure no blurring. In some embodiments, shifting of charge may be performed between just 1-2 pixels to ensure no blurring of the image occurs. The rate of this charge shifting, also called the sensor line rate, can be chosen to accurately match the motion of the image. The total time in the TDI mode of operation may be just one or a few line clock periods, depending on the total illumination pulse time. However, image quality loss due to blurring and the resulting degradation of defect detection would be very significant without providing the TDI-mode of operation.

Sensor mode 2 is high-speed split-readout operation in which illumination is off (i.e. no laser pulse is present). Notably, because the illumination is off, data can be read out from two sides (e.g. sides 203A and 203B of image region 203, FIG. 2A) as fast as the clock signals for the serial registers will allow. During this time, image sensor 110 is not synchronized with image motion 109.

Referring back to FIG. 2A, in one embodiment, an actual illumination region 205 may be slightly smaller than the sensor image region 203. Therefore, when charge shifting occurs during TDI-mode operation, the image will move outside the optical field of view. However, the image is still stored by image region 203 because of the charge stored in the pixels. Therefore, during the high-speed split-readout mode, there would be some blank or lower-signal lines that are first read out before uniformly illuminated image data. This artifact can be compensated for during processing, or ignored if a suitable image frame overlap is chosen that allows for redundancy near the frame edges. Specifically, when the signals are output from the amplifiers, the image can be reconstructed with compensation for illumination effects near the edge of the image frame.

Sensor mode 0 is idle operation in which the sensor image charge (not the object) is static (i.e. stopped). In one embodiment, one set of signals, such as signals of CCD drivers P3a and P3b, can be kept high during the idle operation to provide pre-charging of predetermined pixels and ensure transition between states without losing signal charge or image data at the edge of field. Note that the image sensor needs to rapidly measure charge on each pixel with an accuracy of less than one millivolt. The image sensor may not be able to make such a measurement in the presence of voltage noise in the substrate. To address this issue, moving the charge from pixel to pixel can be discontinued while the readout amplifiers read signals from the serial registers. In one embodiment, the illumination pulse can occur after a period sufficient for at least one charge transfer to occur due to timing uncertainties of the illumination source. The trigger for the sensor to begin TDI-mode operation can be derived from the camera clock or based on optical detection of the illumination pulse. Since the object motion and image sensor line rate are well synchronized, the timing stability of the source can be quite poor and yet allow for a sharp and accurately positioned image to result. After the end of sensor mode 2, image sensor 110 returns to sensor mode 0 (idle mode), and waits for the next synchronization signal and illumination pulse. Note that the processing, buffering, and transport of the collected data from amplifiers 204A and 204B to an external image processing computer (not shown) may proceed during all sensor modes.

Figure 3B:
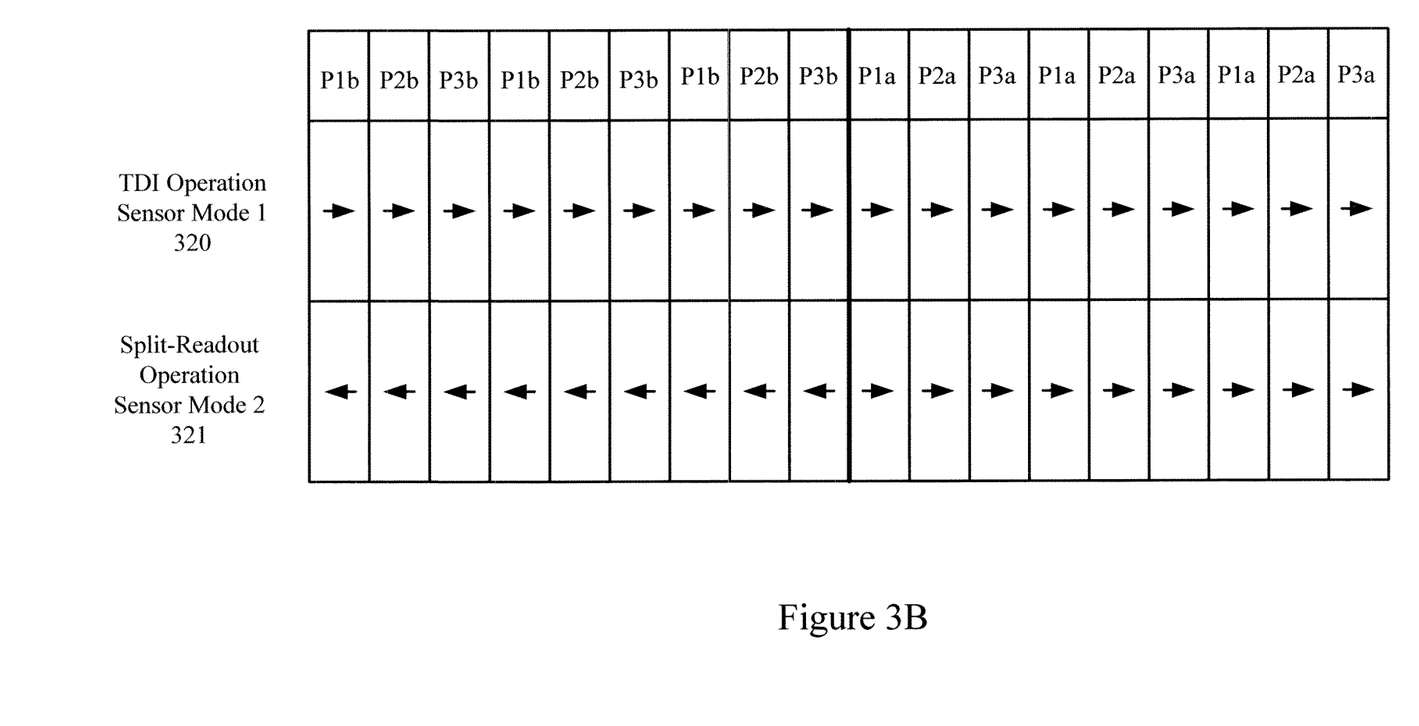
FIG. 3B illustrates how charge is shifted in different directions in the sensor image collection and storage region, based on the sequence of the CCD drive signals.

FIG. 3B illustrates how charge is shifted in different directions based on the sequence of the CCD drive signals. Specifically, during TDI-mode operation (sensor mode 1) 320, the CCD drive signals are sequenced so that charges can be shifted through the pixels all in one direction. In contrast, during split-readout operation (sensor mode 2) 321, the CCD drive signals are sequenced so that the half of the charges are shifted in one direction and the other half of the pixel's charges are shifted in the opposite direction. Note that each CCD drive signal is provided to all the gates in one or more pixel columns of the image region of the sensor array. Thus, the sequence is based on the physical wiring of the sensor. Although 18 columns are shown in FIG. 3B, other embodiments of a sensor array can include fewer or more columns of pixels.

Figure 4:
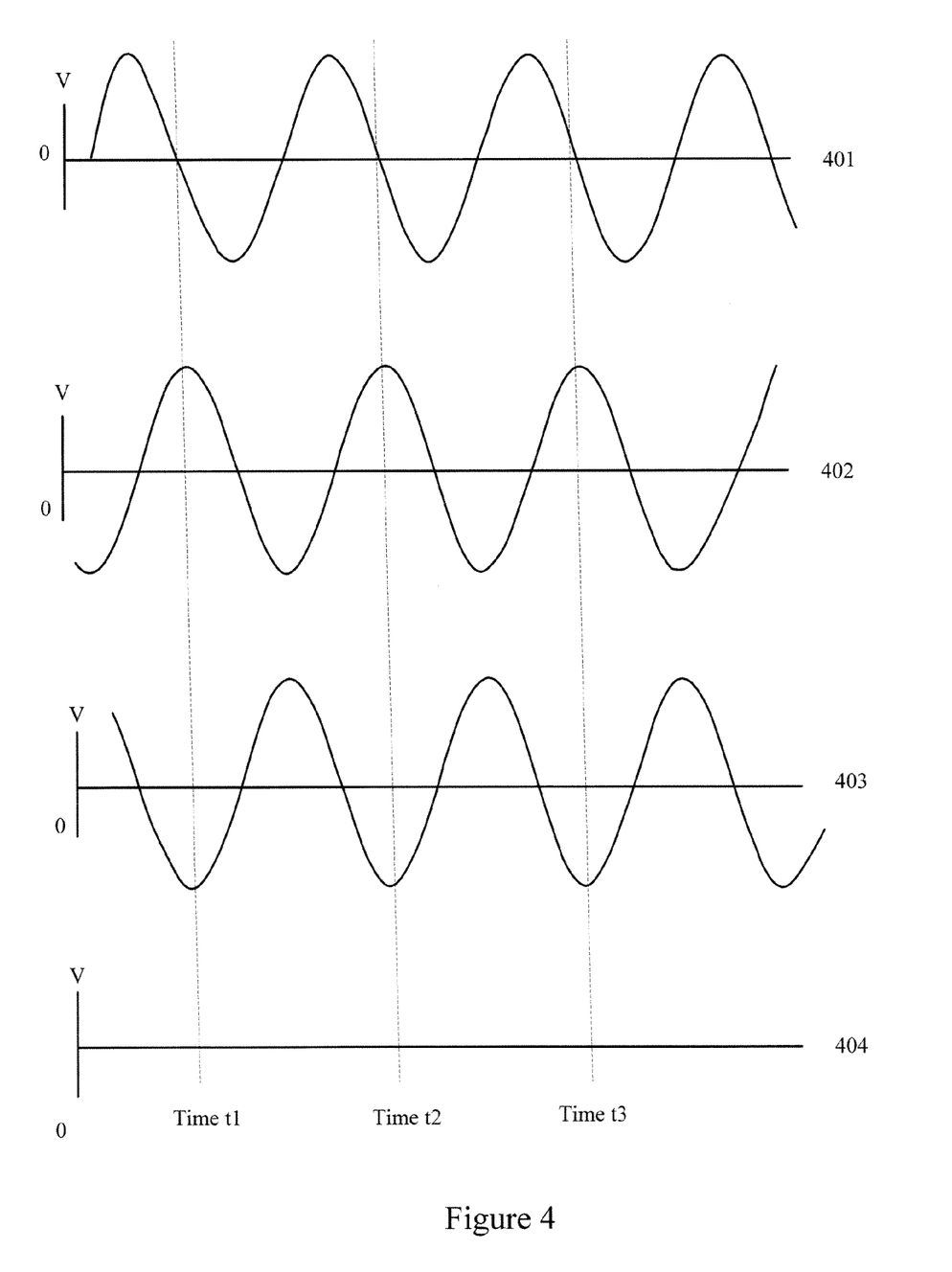
FIG. 4 illustrates exemplary drive signals and relative timing for a three-phase CCD.

In some embodiments, the COD drive signals may be square, as shown in FIG. 3A. In other embodiments, the CCD drive signals may have other shapes. For example, FIG. 4 illustrates sinusoidal drive signals for a three-phase CCD. For example, voltage waveforms 401, 402, and 403 can respectively drive gates 231 and 234, gates 232 and 235, and gates 233 and 236 in image region 203 (see also, FIG. 2A). Notably, these waveform shapes operate at different voltage phases in adjacent gates in such a way to provide a substantially de minimus net voltage fluctuation on ground and DC voltage reference planes, thereby reducing noise. Moreover, transferring charge using a non-square waveform, e.g. sinusoidal, rather than a square waveform generally requires lower peak currents to control the gates. As a result, the peak displacement currents flowing in the substrate are much lower, thereby ensuring lower voltage fluctuations and reduced heat generation in the substrate.

The low levels of voltage fluctuations in the substrate also enable the system to accurately read out the contents of the pixels in the serial register with sufficient sensitivity even when the sensor is transferring charge in the image region. Thus, by using the sinusoidal waveforms, the readout amplifiers may concurrently operate while moving the charge in the image area from one pixel to another. In other embodiments, the CCD drive signals may have other non-square waveform shapes, which can also provide similar benefits to those discussed for sinusoidal waveforms.

In one embodiment, instead of having one pulse per sensor cycle (i.e. sensor modes 0, 1, 2), multiple, grouped pulses (e.g. a strobe-like set of at least two pulses) can be used. After readout, the image can be processed to take into account the multiple, grouped pulses. Specifically, because the location of the object and the illumination timing is known, the measured image can be deconvolved into a corrected "true" image. This type of pulsing and subsequent processing can improve the sensitivity of the original image because at least two samples are provided for each pixel. Specifically, the multiple pulses provide a higher signal to noise ratio because at least twice as much data is provided (compared to a single pulse) with little additional noise (as described above).

Moreover, having two samples for each pixel may be beneficial when a predominantly dark image with a few bright spots (indicating defects, for example) is captured. In this type of image, there is minimal interference with other parts of the image. Two bright spots generated during readout can be deconvolved to determine whether, for example, two bright spots are in fact one defect. This deconvolving would use information including time and image movement speed (because image would move between pulses) to provide the requisite reconstruction.

Note that this multiple, grouped pulse embodiment may also be used to address sensor defect detection. Specifically, if there is a defect on the sensor itself (which would result in missing information on the image), then two samples allow for the inclusion of image information that would otherwise be unavailable. In other words, images over more than one pixel can be collected during the illumination pulses to recover image data at a defective sensor pixel location. This multiple pulse operation could reduce the cost of sensors because increased levels of imperfections can be allowed in sensors while still ensuring the collection of all image information (or substantially all image information in the unlikely event that the two sensor defects coincide with the pixels capturing image data during the multiple, grouped pulses).

As described above, system 100 can advantageously combine certain beneficial properties of TDI readout mode with fast readout capability of pulsed image architectures. Because of the fast readout speed, system 100 can effectively reduce cost of ownership. In addition, system 100 provides for improved resolution of the image for illumination times that would blur when collected with conventional image sensors. In other words, conventional image sensors cannot use long pulse light sources due to image blurring. Notably, long pulse light sources can reduce wafer damage by reducing peak power illumination. Moreover, system 100 can use various CCD drive waveform shapes, including sinusoidal waveforms. These sinusoidal waveforms can be used effectively in high-speed inspection and metrology applications where low noise is critical. In addition, the continuous-clocking technique (i.e. the three sensor modes described above, with the idle mode using fixed voltages in both square-wave and sinusoidal waveform operation) can reduce heat generation and mitigate the negative effects of timing jitter in the control and readout electronics.

Although illustrative embodiments of the invention have been described in detail herein with reference to the accompanying figures, it is to be understood that the invention is not limited to those precise embodiments. They are not intended to be exhaustive or to limit the invention to the precise forms disclosed. As such, many modifications and variations will be apparent to practitioners skilled in this art. For example, in one embodiment, the image sensor could comprise a back-illuminated back-thinned CCD. Back-illuminating a thinned sensor ensures good sensitivity to UV light. In some embodiments, the back-illuminated back-thinned CCD could have a thin boron coating on its light-sensitive back surface in order to increase the lifetime of the device when used with DUV or vacuum UV radiation. The use of boron coatings on back-thinned sensors is described in U.S. Provisional Patent Application 61/622,295 by Chern et al, filed on Apr. 10, 2012. This provisional application is incorporated by reference herein. In some embodiments, the image sensor could comprise an electron-bombarded CCD (EBCCD) sensor. EBCCDs have high sensitivity and low noise for very low light levels as are often encountered in dark-field inspection systems. In some embodiments of the EBCCD, the CCD may be a back-thinned device with a boron coating on its back surface in order to improve the sensitivity of the CCD to low-energy electrons and, hence, improve the image sensor noise and spatial resolution. The use of boron coatings in EBCCDs is described in U.S. Provisional Patent Application 61/658,758 by Chuang et al, filed on Jun. 12, 2012, which is also incorporated by reference herein. Accordingly, it is intended that the scope of the invention be defined by the following claims and their equivalents.

The invention claimed is:

1. A method of operating an image sensor to generate an image of a continuously moving object, the image sensor including a plurality of pixels aligned along a read-out axis, wherein the continuously moving object moves along an axis of movement that is parallel to the read-out axis, the method comprising:
   performing a timed delay integration mode (TDI-mode) operation during an illumination pulse, wherein a plurality of charges are respectively stored by said plurality of pixels of the image sensor, each said charge forming an image region generated by said pulsed illumination reflected from a corresponding fixed point on the continuously moving object, and the plurality of charges are shifted from pixel to pixel only in a first direction along the read-out axis during said TDI-mode operation such that each said charge is shifted along with said corresponding fixed point in a manner that prevents blurring; and
   performing a split-readout operation during a non-illumination period following the TDI-mode operation, wherein first said charges stored by first said pixels of the image sensor are shifted from pixel to pixel in the first direction along the read-out axis while second said charges stored by second said pixels of the image sensor are concurrently shifted from pixel to pixel in a second direction along the read-out axis during the split-readout operation, the second direction being opposite to the first direction.

2. The method of claim 1, wherein the TDI-mode operation is synchronized with the illumination pulse.

3. The method of claim 1, wherein the TDI-mode operation is triggered to start within one clock period of the illumination pulse using electronic or optical synchronization.

4. The method of claim 1, wherein a time of the TDI-mode operation includes a period of the pulsed illumination.

5. The method of claim 1, wherein during the split-readout operation, the image sensor is not synchronized with an image motion.

6. The method of claim 1, wherein performing the split-readout operation includes a parallel readout of a plurality of serial registers.

7. The method of claim 1, further including:
   providing an idle operation between the TDI-mode operation and the split-readout operation.

8. The method of claim 7, wherein providing the idle operation is performed before the TDI-mode operation of the image sensor.

9. The method of claim 1, wherein an illumination interval includes a plurality of illumination pulses extending over one or more TDI line periods.

10. The method of claim 9, further including recovering from a pixel defect of the image sensor based on analyzing pixel outputs corresponding to the plurality of illumination pulses.

11. A system comprising:
   a pulsed illumination source;
   an image sensor including a plurality of pixels aligned along a read-out axis;

optical components configured to direct pulsed illumination from the pulsed illumination source to an object that is continuously moving along an axis of movement, the axis of movement being parallel to the read-out axis, and configured to direct reflected light from the object to the image sensor; and a processor configured to operate the image sensor, a configuration performing a process comprising:

performing a timed delay integration mode (TDI-mode) operation during an illumination pulse, wherein a plurality of charges are respectively stored by said plurality of pixels of the image sensor, each said charge forming an image region generated by said pulsed illumination reflected from a corresponding fixed point on the continuously moving object, and the plurality of charges are shifted from pixel to pixel only in a first direction along the read-out axis during said TDI-mode operation such that each said charge is shifted along with said corresponding fixed point in a manner that prevents blurring; and performing a split-readout operation during a non-illumination period following the TDI-mode operation, wherein first said stored by first said pixels of the image sensor are shifted from pixel to pixel in the first direction along the read-out axis while second said charges stored by second said pixels of the image sensor are concurrently shifted from pixel to pixel in a second direction along the read-out axis during the split-readout operation, the second direction being opposite to the first direction.

12. The system of claim 11, wherein the TDI-mode operation is synchronized with the illumination pulse.

13. The system of claim 11, wherein the TDI-mode operation is triggered to start within one clock period of the illumination pulse using electronic or optical synchronization.

14. The system of claim 11, wherein a time of the TDI-mode operation includes a period of the pulsed illumination.

15. The system of claim 11, wherein during the split-readout operation, the image sensor is not synchronized with an image motion.

16. The system of claim 11, wherein performing the split-readout operation includes a parallel readout of a plurality of serial registers.

17. The system of claim 11, further including:
providing an idle operation between the TDI-mode operation and the split-readout operation.

18. The system of claim 17, wherein providing the idle operation is performed before TDI-mode operation of the image sensor.

19. The system of claim 11, wherein an illumination interval includes a plurality of illumination pulses extending over one or more TDI line periods.

20. The system of claim 19, further including recovering from a pixel defect of the image sensor based on analyzing pixel outputs corresponding to the plurality of illumination pulses.

* * * * *